(12) United States Patent
Ishikura et al.

(10) Patent No.: US 8,992,483 B2
(45) Date of Patent: Mar. 31, 2015

(54) INDWELLING NEEDLE ASSEMBLY AND PROTECTOR

(75) Inventors: Kohzo Ishikura, Osaka (JP); Katsuhiro Hiejima, Osaka (JP); Katsunori Kawai, Osaka (JP)

(73) Assignee: Nipro Corporation, Osaka (JP)

(*) Notice: Subject to any disclaimer, the term of this patent is extended or adjusted under 35 U.S.C. 154(b) by 1209 days.

(21) Appl. No.: 12/078,067

(22) Filed: Mar. 26, 2008

(65) Prior Publication Data
US 2008/0249478 A1 Oct. 9, 2008

(30) Foreign Application Priority Data

Mar. 27, 2007 (JP) .................................. 2007-080815
Jun. 29, 2007 (JP) .................................. 2007-171427

(51) Int. Cl.
*A61M 5/32* (2006.01)
*A61M 25/06* (2006.01)

(52) U.S. Cl.
CPC ......... *A61M 25/0618* (2013.01); *A61M 5/3273* (2013.01)
USPC ............ 604/198; 604/192; 604/197; 604/263

(58) Field of Classification Search
USPC .......................... 604/192, 198, 263, 110, 197
See application file for complete search history.

(56) References Cited

U.S. PATENT DOCUMENTS

| | | | | |
|---|---|---|---|---|
| 5,458,658 A | * | 10/1995 | Sircom | 604/192 |
| 6,117,108 A | | 9/2000 | Woehr et al. | 604/110 |
| 6,203,527 B1 | * | 3/2001 | Zadini et al. | 604/110 |

FOREIGN PATENT DOCUMENTS

| | | |
|---|---|---|
| EP | 0 747 085 A2 | 12/1996 |
| EP | 1 731 192 A2 | 12/2006 |
| JP | 09-099073 A | 4/1997 |
| JP | 2001-514943 A | 9/2001 |
| JP | 2002-210005 A | 7/2002 |
| JP | 2002-248168 A | 9/2002 |
| WO | 99/08742 A1 | 2/1999 |

* cited by examiner

*Primary Examiner* — Kami A Bosworth
*Assistant Examiner* — Imani Hayman
(74) *Attorney, Agent, or Firm* — Kubovcik & Kubovcik

(57) ABSTRACT

An indwelling needle assembly and protector. The indwelling needle assembly has an inner needle, an inner needle hub, an outer needle, an outer needle hub, and a protector for protecting the needle point of the inner needle arranged on the outer periphery of the inner needle so as to be slidable in the axial direction. The protector includes a protecting member in which the needle point of the inner needle is stored and a closing member arranged on the outer periphery of the protecting member so as to be capable of sliding, a displaceable side wall which is capable of being displaced inward so as to close a distal opening of the protecting member, the displaceable side wall being displaced inwardly by the closing member arranged on the outer periphery of the distal end portion of the protecting member.

22 Claims, 8 Drawing Sheets

INDWELLING NEEDLE ASSEMBLY AND PROTECTOR

BACKGROUND OF THE INVENTION

1. Field of the Invention

The present invention relates to an indwelling needle assembly to be pricked into and indwelled in a blood vessel when carrying out fluid infusion or drawing of blood and to a needle protector for protecting a needle point of a needle of an indwelling needle assembly, an injection needle or the like.

2. Description of the Prior Art

When carrying out fluid infusion or drawing of blood for a patient, an indwelling needle including a metallic needle for pricking into the patient's skin (inner needle) and a resin needle (outer needle) for being indwelled in the patient's blood vessel arranged on the outer periphery of the inner needle is used. The inner needle of the indwelling needle has a sharp needle point, and may cause an accident such as erroneous puncture when withdrawing the inner needle from the outer needle to leave only the outer needle indwelled in the patient after use.

So far, when discarding an inner needle after use, procedures such as reinserting the inner needle into a package in which the needle had been stored before use or reinserting the needle point of the inner needle into a cap which had been covering the needle point before use have been taken. However, close attention must also be paid not to cause erroneous puncture with the needle point during such procedures, and hence, these measures cannot successfully reduce the risk of an erroneous puncture.

In order to reduce the probability of erroneous puncture as described above, indwelling needle assemblies provided with an erroneous puncture preventing mechanism, which protects the sharp needle point of the inner needle from being exposed when the inner needle is withdrawn from the outer needle, have started to be widely used in recent years.

As an example of such an erroneous puncture preventing mechanism, there is a protector which is arranged on the inner needle so as to be slidable axially on the needle, and is capable of storing the needle point in the interior thereof. Examples of the protector described above are an indwelling needle assembly provided with a cylindrical protector having a plurality of inwardly urged fingers at a distal end thereof (see Patent Document 1) or an indwelling needle assembly provided with a protector composed of an elastic spring clip having walls at the front and rear (see Patent Document 2, 3 or 4).

The protector in these indwelling needle assemblies has openings at two or more points, that is, on the side of a needle point (distal side) and on the side of a needle root (proximal side) for allowing insertion of the needle, and is fixedly engaged in the interior of an outer needle hub in a state before usage of the indwelling needle. When the inner needle is pulled out from the proximal side of the outer needle after having pricked the indwelling needle into the patient, the protector is maintained in a fixed state on the outer needle hub. Therefore, the needle point of the inner needle passes through the opening on the distal side of the protector, and is stored in the protector for protection. Then, the engagement between the protector and the outer needle hub is released, and the protector is completely pulled out from the outer needle together with the inner needle. The distal end portion of the protector has an inwardly urged portion, so that when pulling out the inner needle, the opening is closed immediately after the needle point has passed through the opening on the distal side and the needle point is prevented from being exposed again from the distal end portion of the protector. Therefore, the distal end portion of the protector is constantly in press-contact with the outer periphery surface of the inner needle in a state before the inner needle is pulled out, which increases a sliding resistance against the movement of the protector on the inner needle and increases a force required for protecting the needle point.

[Patent Document 1] JP-A-9-99073
[Patent Document 2] JP-T-2001-514943
[Patent Document 3] JP-A-2002-248168
[Patent Document 4] JP-A-2002-210005

OBJECTS OF THE INVENTION

Medical personnel normally remove an inner needle with one hand, and hence, it is preferable that the needle point of the inner needle is simultaneously protected with removal of the inner needle from the outer needle or immediately before removal. However, when a force required to protect the needle point is increased, protection of the needle point cannot be done by one hand. Consequently, there is a possibility that the needle point is not protected immediately after removal, and that the protector is not completely slid to a position where the needle point is protected, whereby the needle point injures a blood vessel or skin of a patient when the inner needle is pulled out.

Accordingly, it is an object of the present invention to provide a needle protector and an indwelling needle assembly in which a needle point is protected when the inner needle is removed and requires less force to protect the needle point than protectors and indwelling needle assemblies of the related art. Thus, operation of a protector and indwelling needle assembly by one hand is achieved.

SUMMARY OF THE INVENTION

The inventors of the present application have found that the problems described above are solved by a configuration in which a protector is divided into two members, a protecting member and a closing member, so that an inwardly urging force at the distal end portion of the protector is not applied to the outer peripheral surface of the needle before the inner needle is pulled out.

The present invention provides, (1) An indwelling assembly including an inner needle having a sharp needle point at the distal end thereof and an engaging portion in the vicinity of the distal end; an inner needle hub provided at the proximal end portion of the inner needle; an outer needle arranged on the outer periphery of the inner needle; an outer needle hub provided at the proximal end portion of the outer needle; and a protector for protecting the needle point of the inner needle arranged on the outer periphery of the inner needle so as to be axially slidable, in which the protector includes a protecting member having an inner space which allows storage of the needle point of the inner needle and being slidable axially on the inner needle; and a closing member arranged on the outer periphery of the protecting member so as to be slidable from the proximal end of the protecting member to the distal end thereof, in which the protecting member includes a distal opening which allows insertion of the inner needle and a proximal opening which allows insertion of an inner needle body but prevents passage of the engaging portion, a displaceable side wall which is capable of being displaced inward so as to close the distal opening when the needle point is stored in the inner space of the protecting member and provided at the distal end portion of the protecting member, the displaceable side wall being displaced inward by the closing member arranged on the outer periphery of the distal end portion of the protecting member, in which the closing member is arranged on the outer periphery of the proximal end portion on which the displaceable side wall of the protecting member is not provided before the needle point is stored in the inner space of the protecting member, and is slid on the outer periphery of the protecting member toward the distal side and is arranged on the outer periphery of the distal end portion on which the displaceable side wall of the protecting member is provided when the needle point is stored in the inner space of the protecting member, and in which the protector is arranged in the outer needle hub before the needle point of the inner needle is stored in the inner space of the protecting member and the inner peripheral surface of the outer needle hub and the closing member are fixedly engaged, the engagement between the outer needle hub and the closing member is maintained until the inner needle is pulled out from the outer needle toward the proximal side and the protecting member is moved toward the proximal side together with the inner needle by engagement between the engaging portion of the inner needle and the proximal opening of the protecting member, whereby the closing member is slid and arranged on the outer periphery of the distal end portion of the protecting member, and the engagement between the outer needle hub and the closing member is released when the closing member is locked by locking means provided at the distal end portion of the protecting member, so that the separation of the protector from the interior of the outer needle hub is enabled.

(2) The indwelling needle assembly according to (1), in which the protecting member of the protector includes a proximal wall having the proximal opening and a distal wall having the distal opening; and side walls formed integrally with the proximal wall and the distal wall and extending in the axial direction of the needle, and the displaceable side wall is provided on part of at least one of the side walls.

(3) The indwelling needle assembly according to (2), in which the protecting member of the protector includes a pair of opposing side walls, and the distal end portion of one of the side walls is the displaceable side wall.

(4) The indwelling needle assembly according to (2), in which the protecting member of the protector includes four side walls which surround the needle point from four sides, and a pair of the displaceable side walls are provided at a pair of distal end portions of opposing side walls, (5) The indwelling needle assembly according to (1), in which the closing member of the protector includes an opening having an inner diameter slightly smaller than the inner diameter required for allowing insertion of the proximal end of the protecting member, and is arranged on the outer periphery of the proximal end portion of the protecting member in a state of being urged inward.

(6) The indwelling needle assembly according to (5), in which the closing member of the protector is a partly cut annular member.

(7) The indwelling needle assembly according to (5), in which the closing member of the protector is an annular member formed of an elastic material.

(8) The indwelling needle assembly according to (5), in which the locking means provided at the distal end portion of the protecting member is at least one groove portion which allows fitting of the closing member when being contracted by an urging force.

(9) The indwelling needle assembly according to (1), in which the closing member of the protector is an annular member having an opening having an inner diameter which allows insertion therein of the proximal end of the protecting member, and being arranged on the outer periphery of the proximal end portion of the protecting member in a natural state.

(10) The indwelling needle assembly according to (9), in which the locking means provided at the distal end portion of the protecting member is a first claw projecting outward toward the proximal side and a second claw provided on the proximal side of the first claw and projecting outward toward the distal side.

(11) The indwelling needle assembly according to (1), in which engagement fixation between the inner peripheral surface of the outer needle hub and the closing member before the needle point of the inner needle is stored in the inner space of the protecting member is achieved by the closing member being fitted into an annular recess formed on the inner peripheral surface of the outer needle hub.

(12) The indwelling needle assembly according to (1), in which engagement fixation between the inner peripheral surface of the outer needle hub and the closing member before the needle point of the inner needle is stored in the inner space of the protecting member is achieved by the closing member being engaged with an annular projection formed on the inner peripheral surface of the outer needle hub on the proximal side with respect to the closing member.

(13) A protector for protecting a needle point including: a protecting member having an inner space for allowing storage of a needle point and openings provided on a distal side and a proximal side for allowing insertion of the needle and being slidable on the needle axially of the needle; and a closing member arranged on the outer periphery of the protecting member so as to be slidable from the proximal end to the distal end, in which the protecting member includes a displaceable side wall provided at the distal end portion thereof so as to be displaceable inward thereby closing the opening on the distal side when the needle point is stored in the inner space of the protecting member, and the displaceable side wall is displaced inward by the closing member arranged on the outer periphery of the distal end portion of the protecting member.

(14) The protector according to (13) in which the protecting member includes: a proximal wall having a proximal side opening and a distal wall having a distal side opening; and side walls formed integrally with the proximal wall and the distal wall and extending axially of the needle, and the displaceable side wall is provided on part of at least one of the side walls.

(15) The protector according to (14), in which the protecting member includes a pair of opposing side walls, and a distal end portion of one of the side walls is the displaceable side wall.

(16) The protector according to (14), in which the protecting member includes four side walls which surround the needle point from four sides, and a pair of an opposing side walls is provided with a pair of displaceable side walls at the distal end portions thereof.

(17) The protector according to (13), in which the closing member is arranged on the outer periphery of the proximal end portion of the protecting member where the displaceable side wall is not provided before the needle point is stored in the inner space of the protecting member, and is slid on the outer periphery of the protecting member toward the distal side and is arranged on the outer periphery of the distal end portion where the displaceable side wall is provided when the needle point is stored in the inner space of the protecting member, and in which the protecting member is provided at the distal end portion thereof with locking means which is capable of preventing further sliding movement when the closing member is arranged on the outer periphery of the distal end portion and maintaining the displaceable wall in a state of being displaced inward.

(18) The protector according to (13), in which the closing member is provided with an opening having an inner diameter for allowing insertion of the proximal end of the protecting member, and is arranged on the outer periphery of the proximal end portion of the protecting member in a natural state.

(19) The protector according to (18), in which the closing member is an annular member, and the locking means are a first claw projecting outward toward the proximal side and a second claw provided on the proximal side of the first claw and projecting outward toward the distal side.

(20) The protector according to (13), in which the closing member includes an opening having an inner diameter slightly smaller than the inner diameter required for allowing insertion of the proximal end of the protecting member, and is arranged on the outer periphery of the proximal end portion of the protecting member in a state of being urged inward by the inner periphery thereof being expanded outward.

(21) The protector according to (20), in which the closing member is an annular member formed of an elastic material, and the locking means is at least one recess which allows the closing member contracted by an urging force to fit therein.

(22) The protector according to (20), in which the closing member is a partly cut annular member, and the locking means is at least one recess which allows the closing member contracted by the urging force to fit therein.

ADVANTAGES OF THE INVENTION

The indwelling needle assembly according to the present invention includes a protector composed of two members, a protecting member and a closing member, so that an inward urging force is not applied directly to the outer peripheral surface of the needle. Therefore, sliding resistance of the protector, which is slid on the inner needle when pulling out the inner needle, is lowered. Operation of the indwelling needle assembly is carried out with one hand. When arranging the protector on the inner needle before use, the inward urging force of the protector is not applied directly to the outer peripheral surface of the needle. Therefore, it is not necessary to insert the inner needle into the opening of the protector against the urging force, and hence smooth arrangement is achieved.

DESCRIPTION OF PREFERRED EMBODIMENTS

Figure 1:
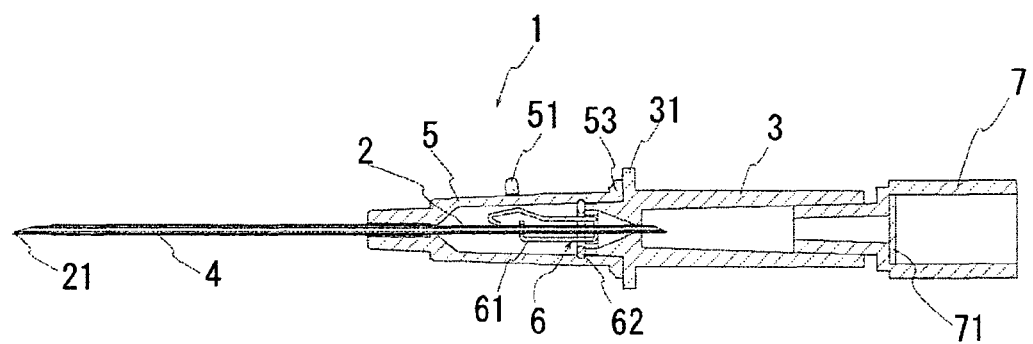
FIG. 1 is a vertical cross-sectional view illustrating an example of an indwelling needle assembly according to the present invention in a state before an inner needle is pulled out.

Referring now to the drawings, preferred embodiments of the present invention will be described in detail. However, the present invention is not limited thereto.

As shown in FIG. 1, an indwelling needle assembly 1 according to the present invention includes an inner needle 2 having a sharp needle point 21 at a distal end thereof, an inner needle hub 3 provided at a proximal end portion of the inner needle 2, an outer needle 4 arranged on the outer periphery of the inner needle 2, an outer needle hub 5 provided at the proximal end portion of the outer needle 4 and a protector 6 arranged on the outer periphery of the inner needle 2. In the indwelling needle assembly 1 of the present invention, the distal side represents the needle point 21 side to be pricked (inserted) into a patient (left side in the drawing), and the proximal side represents a needle root side to be connected to a syringe or a tube (right side in the drawing).

The inner needle 2 is a hollow needle and may be formed of, for example, stainless steel, aluminum or an aluminum alloy, or titanium or a titanium alloy. However, in view of workability and cost, stainless steel is preferable. Although the inner needle 2 has the sharp needle point 21 at the distal end thereof, the shape of the sharp needle point is not specifically limited as long as it reduces a pricking resistance against a patient.

As shown in FIG. 8, an engaging portion 22 is formed in the vicinity of the distal end of the inner needle 2. The engaging portion 22 is a portion of the surface of the outer periphery of the inner needle 2 with an enlarged diameter which does not allow passage through a proximal opening 613 of a protecting member 61 of the protector 6 (described below). The engaging portion 22 may be an annular widened portion which is an outer peripheral surface of the inner needle 2 widened in diameter along the circumferential direction, or may be a projection provided at a part of or a plurality of positions on the needle in the circumferential direction. The position where the engaging portion 22 is to be provided is where the needle point 21 of the inner needle 2 is stored in an inner space 611 of the protecting member 61. The engaging portion 22 engages a proximal wall 614 at a position of the proximal opening 613 of the protecting member 61 of the protector 6 (described below). The engaging portion 22 is formed by crimping or the like of the inner needle 2.

The inner needle hub 3, provided at the proximal end portion of the inner needle 2, is a substantially cylindrical hollow member, and is fixed to the proximal end portion of the inner needle 2 by fitting, caulking, bonding by melting or with an adhesive agent, or a combination thereof. The inner needle hub 3 is formed of thermoplastic resin or the like, and is formed by injection molding or the like. The inner needle hub 3 is preferably formed of a visible transparent resin, a colored transparent resin or a translucent resin so that flash back of blood can be observed when the inner needle 2 is pricked into a patient.

Preferably, an inner needle cap 7 provided with an air-ventilation filter 71 is connected to the proximal side of the inner needle hub 3. The air-ventilation filter 71 allows passage of gases and prevents passage of liquids, and may be formed of, for example, a sintered porous member obtained by sintering a high polymer material such as polyethylene and a material containing a hydrophilic, water-soluble, or water absorbent polymer, a hydrophobic non-woven fabric and porous member. By including the air-ventilation filter 71, flashback of blood when the inner needle 2 is pricked into the patient is promoted, and blood flowing into the interior of the inner needle 2 by the flashback is prevented from leaking to the outside of the indwelling needle assembly. In addition, since air ventilation is blocked when the air-ventilation filter 71 comes into contact with blood, entry of air from the outside is prevented. The air-ventilation filter 71 may be provided directly in the interior of the proximal end portion of the inner needle hub 3.

The outer needle 4 has a hollow structure, and is formed of a material having a flexibility which reduces the probability of damaging a blood vessel wall when being indwelled in the blood vessel of a patient. Preferable materials of the outer needle 4 are, for example, soft resins such as ethylene-tetrafluoroethylene copolymer, polyurethane, polyether nylon resin or polypropylene. The outer needle 4 may have visibility toward the interior thereof entirely or partly, or may be provided with an imaging function by blending an X-ray contrast agent, such as barium sulfate or barium carbonate, in the material.

Preferably, the distal end of the outer needle 4 is formed into a tapered shape being gradually reduced in outer diameter toward the distal end in order to reduce resistance when being pricked into the patient's blood vessel together with the inner needle 2. The outer needle 4 may be provided with one or more holes at a portion in the vicinity of the distal end thereof so as to ensure efficient passage of a fluid inside the outer needle.

The outer needle hub 5 provided at the proximal end portion of the outer needle 4 is a substantially cylindrical hollow member, like the inner needle hub 3, and is fixed to the proximal end portion of the outer needle 4 by fitting, caulking, bonding by melting or with adhesive agent, or a combination thereof. The material and the method of molding of the outer needle hub 5 are the same as those of the inner needle hub 3. An operating projection 51 to facilitate operation to prick the inner needle 2 and the outer needle 4 into the patient's blood vessel, may be formed on the outer peripheral surface of the outer needle hub 5. A female luer taper 52 or a flange 53 may be formed on the proximal end portion of the outer needle hub 5 for arranging the inner needle hub 3 or connecting medical equipment such as a tube or a connector, described later.

Figure 2:
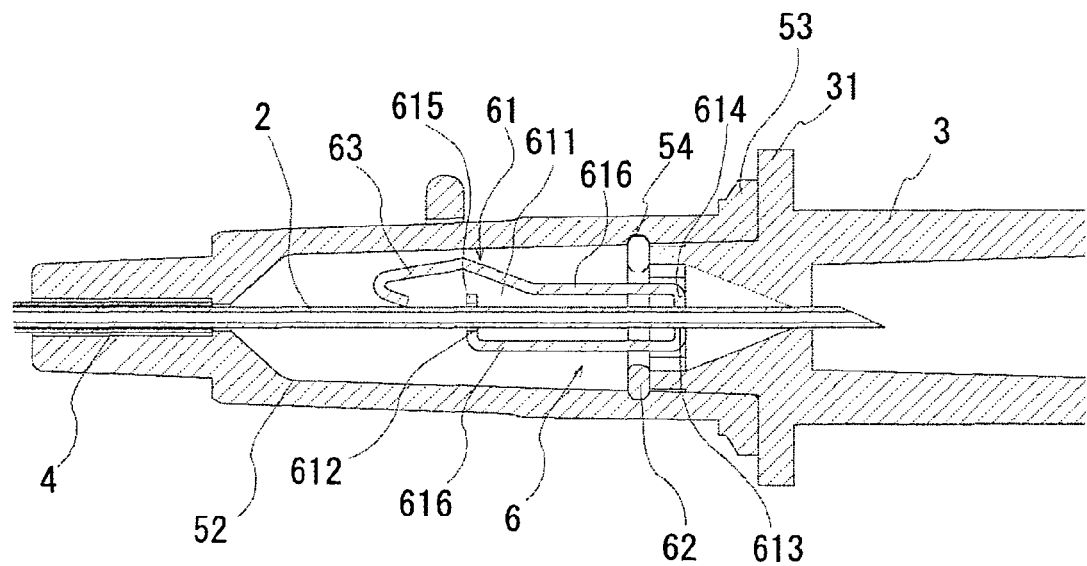
FIG. 2 is an enlarged vertical cross-sectional view of a protector portion of the indwelling needle assembly shown in FIG. 1.

The protector 6 for protecting the needle point 21 of the inner needle 2 is arranged on the outer periphery of the inner needle 2. The protector 6 according to the present invention includes a protecting member 61 and a closing member 62, as shown in FIG. 2. The protecting member 61 includes an inner space 611 which allows storage of the needle point 21 of the inner needle 2, and is capable of sliding axially on the outer periphery of the inner needle 2 in a state in which the inner needle 2 is inserted into a distal opening 612 and a proximal opening 613 of the protecting member. The closing member 62 is arranged on the outer periphery of the protecting member 61, and is capable of sliding on the protecting member 61 from a proximal end portion to a distal end portion thereof.

The protecting member 61 includes a proximal wall 614 having the proximal opening 613, a distal wall 615 having the distal opening 612 and side walls 616 formed integrally with the proximal wall 614 and the distal wall 615 and extending axially of the inner needle 2. The inner space 611, which allows storage of the needle point 21 of the inner needle 2, is defined by the proximal wall 614, the distal wall 615 and the side walls 616. The inner space 611 may be a space which is blocked completely from the outside, or may be a partially open space, as shown in FIGS. 3 to 7.

The shape of the protecting member 61 is not specifically limited as long as it allows insertion of the inner needle 2 into the distal opening 612 and the proximal opening 613 and allows storage of the needle point 21 in the inner space 611. However, the proximal opening 613 has a size which allows passage of a main body of the inner needle 2 and prevents passage of the engaging portion 22 of the inner needle 2, and which allows engagement of the inner needle 2 with the proximal wall 614 at the proximal opening 613 in order to prevent the needle point 21 stored in the inner space 611 from dropping off from the proximal opening 613 toward the proximal side. The distal opening 612 does not have to be a hole formed through the distal wall 615, and may be a groove provided inside the end portion of the distal wall 615 for locating the inner needle 2. In addition, although the protecting member 61 of the present invention is divided into the proximal end portion and the distal end portion, the boundary therebetween is not specifically limited to the axial midsection of the protecting member 61, and may be changed as needed.

As detailed examples of the protecting member 61, there are those having configurations as shown in FIGS. 2 to 7. The protecting members 61 shown in these drawings include the distal wall 615 and the proximal wall 614 each formed into a square plate shape and a pair of the side walls 616 opposed to each other and extending from two opposed ends of the proximal wall 614. One of the side walls 616 has a plate shape, and is formed integrally with the proximal wall 614 at one end thereof and integrally with the distal wall 615 at the other end thereof, so that the proximal wall 614 and the distal wall 615 are arranged so as to oppose to each other. The other side wall 616 is also formed into a plate shape and is formed integrally with the proximal wall 614 at one end thereof and is provided with a displaceable side wall 63 at a part of the distal end portion of the side wall 616.

Figure 3:
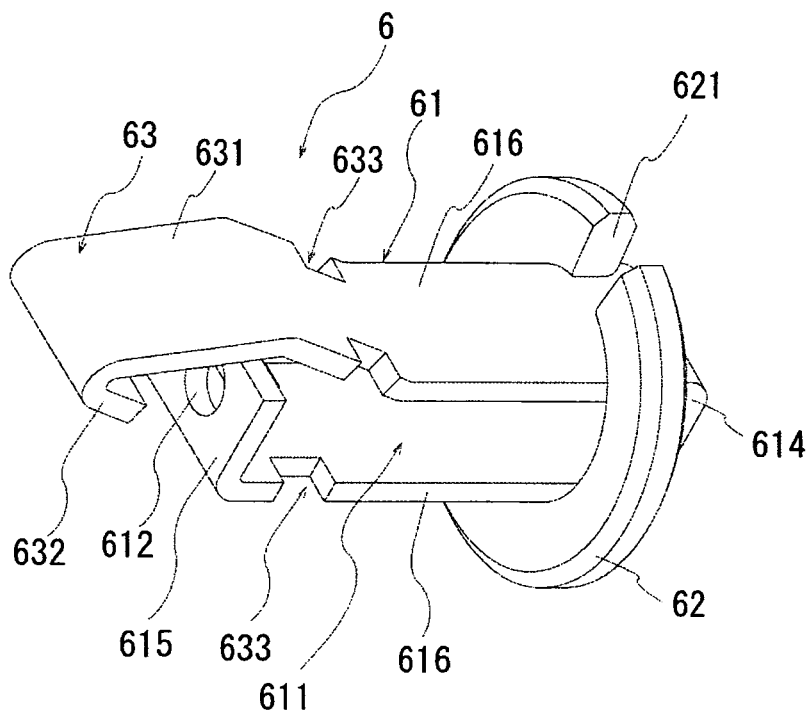
FIG. 3 is a perspective view illustrating an example of the protector in the indwelling needle assembly according to the present invention in a state before a needle point is stored.

The displaceable side wall 63 is provided at the distal end portion of the protecting member 61, and is displaced inwardly so as to close the distal opening 612 formed through the distal wall 615 when the needle point 21 of the inner needle 2 is stored in the inner space 611 of the protecting member 61. As shown in FIG. 3, for example, the displaceable side wall 63 includes a body portion 631 continuing from the side wall 616 in a state of extending outward and a closing portion 632 continuing on the distal side of the body portion 631. The body portion 631 is displaced inwardly toward the needle by application of an external force, that is, is capable of deflecting or bending and, when the body portion 631 is bent inward, the closing portion 632 closes the distal opening 612 of the distal wall 615. To close the distal opening 612, the closing portion 632 does not necessarily have to seal the distal opening 612, and may close the distal opening 612 so as to prevent the needle point 21 of the inner needle 2 stored in the inner space 611 from the distal side of the protecting member 61 from projecting again therefrom.

In addition to the pair of opposing side walls shown in the drawing, the side wall 616 may be four plate-shaped side walls which surround the needle point 21 from four sides, and provide the protecting member 61 with a substantially square pole shape. The displaceable side wall 63 may be provided over the entire part of the distal end portion of one of the side walls 616 (shown in the drawings), or may be provided partly at the distal end portion of one of the side walls 616, (not shown in the drawings). Alternatively, a plurality of displaceable side walls 63 may be provided on a plurality of respective side walls 616.

Figure 4:
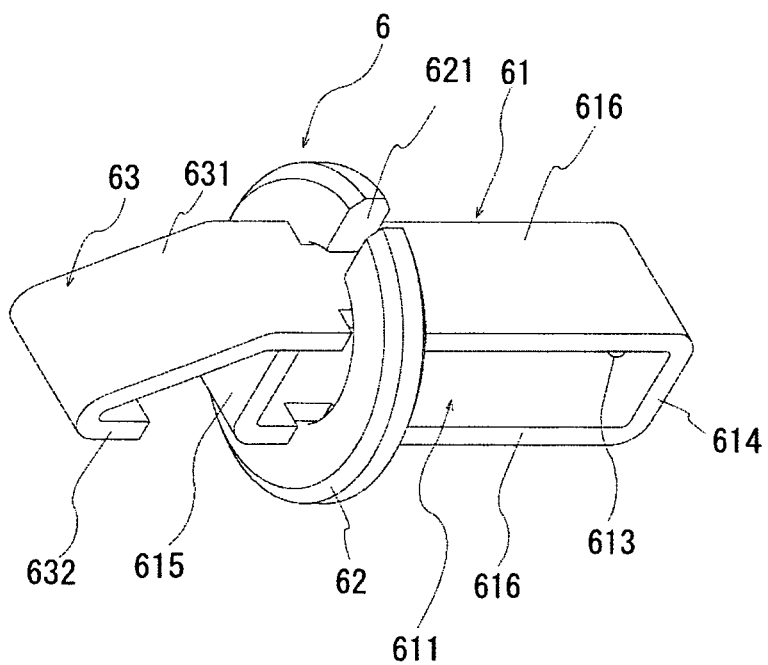
FIG. 4 is a perspective view of the protector shown in FIG. 3 in a state in which the needle point is stored.

Inward displacement of the displaceable side wall 63 is achieved by the closing member 62. The displaceable side wall 63 is displaced inwardly when the closing member 62, slidably arranged on the outer periphery of the protecting member 61, slides on the outer periphery to the distal end portion of the protecting member 61. The displaceable side wall 63 closes the distal opening 612 so as to prevent the needle point 21 of the inner needle 2 from projecting therefrom. The closing member 62 is normally arranged on the outer periphery of the proximal end portion of the protecting member 61 where the displaceable side wall 63 is not provided, as shown in FIG. 3, before the needle point 21 is stored in the inner space 611. The closing member 62 slides on the outer periphery of the protecting member 61 toward the distal side when the needle point 21 is stored in the inner space 611. The closing member 62 is positioned on the outer periphery of the distal end portion where the displaceable side wall 63 is provided as shown in FIG. 4. In the drawing, the proximal end portion of the protecting member 61 represents a portion on the proximal side with respect to the distal end portion.

As other shapes of the protecting member 61 of the present invention, the side wall 616 may be formed into a cylindrical shape so as to store the inner needle 2 completely, or two or more side walls may be formed into a substantially cylindrical shape. The outer periphery of the cross section of the side wall 616 portion of the protecting member 61 taken perpendicularly to the axis thereof may be a polygonal shape, in addition to a square shape and a circular shape shown in the drawings. The shape of the outer periphery of the cross section of the side wall 616 portion of the protecting member 61 taken perpendicularly to the axis thereof and the shape of the inner periphery of the closing member 62 do not necessarily have to be the same. However, the closing member 62 needs to have an inner diameter and a shape which allows sliding movement at a low sliding resistance on the outer periphery of the protecting member 61.

The closing portion 632 of the displaceable side wall 63 of the protecting member 61 is capable of effectively preventing the needle point 21 from projecting from the distal side of the protecting member 61 by being provided so as to project from the distal end portion of the displaceable side wall 63 toward the proximal side.

The protecting member 61 is preferably formed of materials suitable for deforming (inwardly displacing) the displaceable side wall 63 which is displaced inwardly by working thereon, such as metallic materials including stainless steel, aluminum or an aluminum alloy, titanium or a titanium alloy and copper or a copper based alloy, polyolefins including polyethylene, polypropylene, polybutadiene and ethylene-vinyl acetate copolymer, polyesters including polyethylene terephthalate and polybutylene terephthalate, polyvinyl chloride, polyurethane, polystyrene, polymethylmethacrylate, polycarbonate, polyamide, and various resin materials including acryl-based resin, ABS resin, ionomer, polyacetal, polyphenylene sulfide, and polyether ether ketone.

The protecting member 61 formed of a material as listed above may be formed by joining a resin material formed by injection molding or the like, or a metallic material formed by bending. The joining method in this case is not specifically limited and may be, for example, caulking, concavity and convexity engagement, bonding with an adhesive agent and melting. The protecting member 61 may also be formed by combining two or more of those materials. For example, by attaching a member formed of a hard material such as a ceramic on the inner wall of the displaceable side wall 63, the strength of the displaceable side wall 63 is enhanced and breakage due to the displacement may be prevented. The proximal end portion of the protecting member 61 must have a strength which resists deformation so as to prevent direct application of the urging force on the inner needle 2 in a case in which the closing member 62 arranged on the outer periphery is arranged in a state of being urged inward as described later.

The closing member 62 arranged on the outer periphery of the protecting member 61 has an inner diameter and an inner peripheral shape so as to allow sliding movement on the outer periphery of the protecting member 61 as described above. The closing member 62 is formed of, a polyolefin including polyethylene, polypropylene, polybutadiene and ethylene-vinyl acetate copolymer, polyesters including polyethylene terephthalate and polybutylene terephthalate, polyvinyl chloride, polyurethane, polystyrene, polymethylmethacrylate, polycarbonate, polyamide, and various resin materials including acryl-based resin, ABS resin, ionomer, polyacetal, polyphenylene sulfide, and polyether ether ketone, various metallic materials such as stainless steel, aluminum or aluminum alloy, titanium or titanium alloy and copper or copper based alloy, or a hard material such as ceramic. The closing member 62 may also be formed of rubber materials such as natural rubber, isoprene rubber or butadiene rubber, or an elastic material such as thermoplastic elastomer. The closing member 62 is formed into an annular shape or a partly cut annular shape by injection molding or the like.

As an example of the closing member 62, there is a partly cut annular member as shown in FIG. 3 and FIG. 4. The closing member 62 as shown in FIG. 3 and FIG. 4 is formed with an opening having an inner diameter slightly smaller than the inner diameter required for allowing insertion of the proximal end portion of the protecting member 61, and is arranged on the outer periphery of the proximal end portion of the protecting member 61 in a state in which a cut area 621 is expanded. The closing member 62 as described above is formed of a material having rigidity which generates an inward urging force to close the cut area 621. Therefore, the closing member 62 is expanded at the cut area 621 when the closing member 62 is arranged on the outer periphery of the proximal end portion of the protecting member 61 in the state of being urged inward as shown in FIG. 3, and when the closing member 62 is slid toward the distal end as shown in FIG. 4 to be arranged on the outer periphery of the distal end portion of the protecting member 61, the urging force thereof causes the displaceable side wall 63 to be displaced inward.

Preferably, the closing member 62 is prevented from further distal sliding movement by a locking means provided on the outer periphery of the protecting member 61. The locking means holds the protecting member 61 in a state in which the displaceable side wall 63 is displaced inward. The locking means may be, for example, a groove portion or area 633 provided on the displaceable side wall 63 as shown in the drawings so that the closing member 62 is fitted and locked by being contracted inward. At least one such groove area portion 633 is provided on the outer periphery of the distal end portion of the protecting member 61, and as shown in the drawings, by the provision of a plurality of the groove portions 633, the closing member 62 is contracted significantly inward and is reliably locked on the protecting member 61 so as not to be capable of sliding. With the provision of the locking means as described above, the state in which the distal opening 612 is closed by the closing portion 632 may be maintained so that the needle point 21 is stored in the inner space 611 of the protecting member 61 and is prevented from projecting from the distal side of the protecting member 61.

Figure 5:
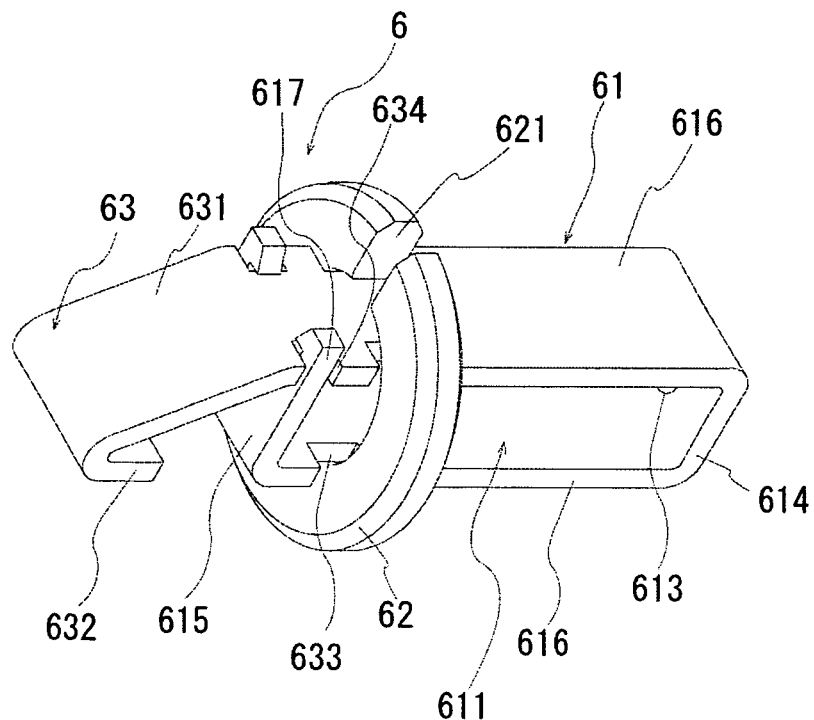
FIG. 5 is a perspective view illustrating another example of the protector in the indwelling needle assembly according to the present invention in a state before the needle point is stored.

The protecting member 61 may further be provided with a locking mechanism for maintaining the state in which the distal opening 612 is closed by the closing portion 632. As an example of the locking mechanism, there is a groove portion or area 634 provided on the displaceable side wall 63 of the protecting member 61 for engaging projections 617 provided on the distal wall 615, as shown in FIG. 5. With the provision of the locking mechanism as described above, the displaceable side wall 63 is held further reliably in a state of being inwardly displaced, and the needle point 21 stored in the inner space 611 of the protecting member 61 is effectively prevented from a risk of projecting from the distal side of the protecting member 61.

Figure 6:
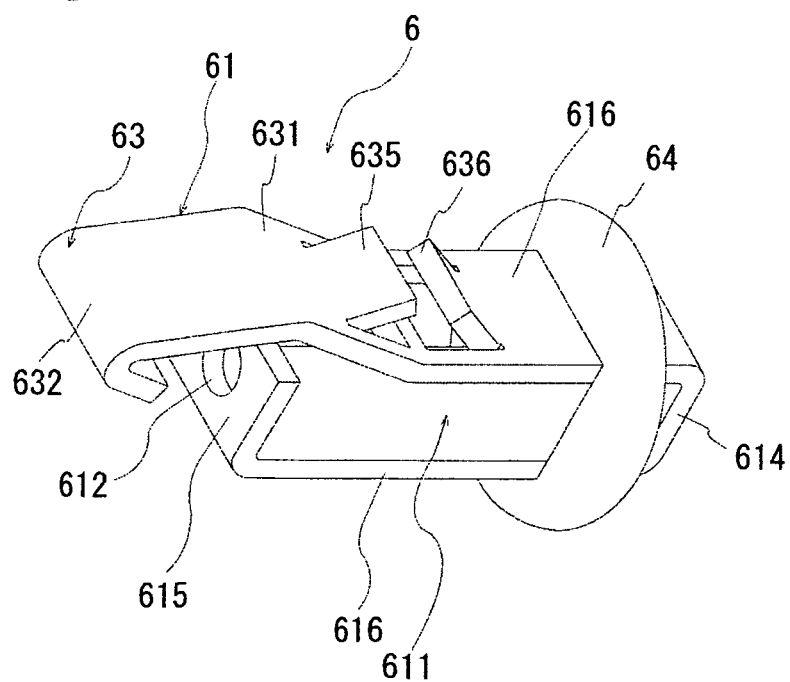
FIG. 6 is a perspective view illustrating another example of the protector in the indwelling needle assembly according to the present invention in a state before the needle point is stored.
Figure 7:
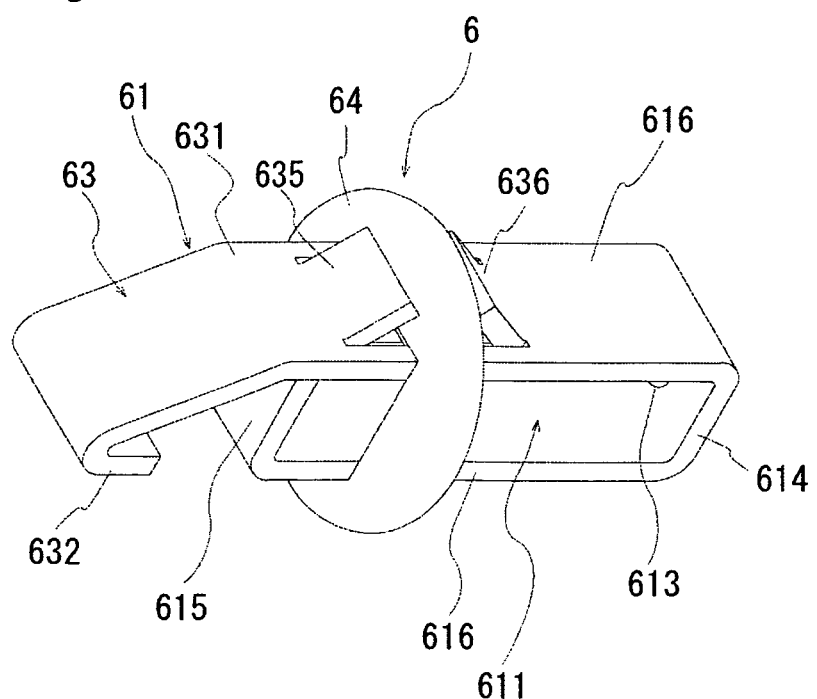
FIG. 7 is a perspective view illustrating the protector shown in FIG. 6 in a state after the needle point is stored.

FIG. 6 is a perspective view illustrating another example of the protector in the indwelling needle assembly according to the present invention in a state before the needle point is stored. FIG. 7 is a perspective view of the protector shown in FIG. 6 in a state after the needle point is stored.

The closing member according to the present invention may be the closing member 64 which is an annular member as shown in FIG. 6 and FIG. 7. The closing member 64 includes an opening having an inner diameter which allows insertion of the proximal end portion of the protecting member 61, and is arranged on the proximal end portion of the protecting member 61 in a natural state that is not biased inwardly. The closing member 64 shown in the drawings is an annular member having a circular outer periphery and a square inner periphery so as to match the outer peripheral shape of the cross section of the side wall 616 portion of the protecting member 61 taken perpendicularly to the axis thereof. However, these shapes are not limited thereto, and the inner periphery may be any shape as long as it allows axial sliding movement on the outer periphery of the protecting member 61. For example, the inner periphery may be a circular shape or a polygonal shape. Although the thickness of the closing member 64 is not specifically limited, it is required to have sufficient rigidity which allows axial sliding movement on the outer periphery of the protecting member 61.

A locking means for holding the closing member 64 on the protecting member 61 in a state in which the displaceable side wall 63 is displaced inward includes, for example, a claw 635 projected outward toward the proximal side and a claw 636 provided on the proximal side of the claw 635 so as to project outward toward the distal side, as shown in the drawings. The closing member 64 slides on the outer periphery of the protecting member 61 from the proximal end portion to the distal end portion, climbs over the claw 636 while urging the same inward, stops sliding when it comes into contact with the projecting end of the claw 635, and is locked between the claw 635 and the claw 636. The claw 636 is released from the urging force from the closing member 64 and is restored to its original position.

Another closing member 64 may be an annular member formed of an elastic material. In the same manner as the closing member 62 which is the partly cut annular member, the closing member 64 includes an opening having an inner diameter slightly smaller than the inner diameter required for allowing insertion of the proximal end portion of the protecting member 61, and is arranged on the outer periphery of the proximal end portion of the protecting member 61 in a state in which the inner periphery is expanded outward and hence is urged inward. Therefore, the closing member 64 causes the displaceable side wall 63 to be displaced inward by an inward urging force when slid on the outer periphery to the distal end portion of the protecting member 61. The closing member 64 in this configuration is preferably fitted into the groove portion 633 provided on the outer periphery of the distal end portion of the protecting member 61 by being contracted inward and is prevented from further sliding movement in the same manner as the closing member 62, i.e., the partly cut annular member.

Since the locking means provided on the closing member 64 is adapted to hold the closing member 64 in a state in which the displaceable side wall 63 is displaced inward, it is basically provided on the displaceable side wall 63. However, when the locking means includes the claws 635 and 636, the claw 636 on the proximal side may be provided on the distal side of the side wall 616. The locking means may also be provided on the distal end portion of the side wall 616 which does not have the displaceable side wall 63 at a position opposing the displaceable side wall 63.

The protecting member 61 may be provided with a second locking means for locking the closing members 62 and 64 on the proximal end portion of the protecting member 61 for maintaining the state in which the closing members 62 and 64 are arranged on the outer periphery of the proximal end portion of the protecting member 61 before the needle point 21 of the inner needle 2 is stored in the inner space 611. As an example of the second locking means described above, a pair of claws such as the claws 635 and 636 are exemplified. When the closing member 62 configured with the partly cut annular member is used, a projection to be clamped in the cut area 621 by further expanding the cut area 621 may be provided. When the closing member 64 formed of the annular elastic material is used, a projection which expands the inner peripheral surface may be provided to be locked on the protecting member 61 by the inward urging force of the closing member 64.

The second locking means is preferably one which is easily released from a locked state and different from the locking means provided at the distal end portion of the protecting member 61 as described above. Therefore, when a pair of claws is employed as the second locking means, it is preferable to minimize the height of the claw on the distal side while maintaining its function. When a projection is employed, it is preferable to form the distal side into a tapered shape. With the provision of the second locking means as described above, pricking the needle point 21 into the patient in a state in which the protector 6 is arranged on the inner needle 2 is easily performed.

The indwelling needle assembly 1 according to the present invention is arranged in such a manner that the outer needle 4 is arranged on the outer periphery of the inner needle 2 so that the needle point 21 of the inner needle 2 is projected from the distal side in a state before puncture as shown in FIG. 1, and the distal end portion of the inner needle hub 3 is inserted into the proximal end portion of the outer needle hub 5. An annular flange 31 is provided on the outer periphery of the inner needle hub 3, and insertion of the inner needle hub 3 into the outer needle hub 5 is stopped by the flange 31 contacting the flange 53 of the outer needle hub 5 at a position where the needle point 21 of the inner needle 2 projects from the distal side of the outer needle 4.

The protector 6 according to the present invention is arranged inside the outer needle hub 5 in a state before puncture of the indwelling needle assembly 1, as shown in FIG. 1. Therefore, a probability that an operator will unintentionally slide the protector 6 by mistake when handling the indwelling needle assembly 1 is reduced.

The inner peripheral surface of the outer needle hub 5 is provided with means for engaging the closing member 62 of the protector 6 so that the protector 6 is fixedly engaged in the interior of the outer needle hub 5 until the needle point 21 of the inner needle 2 is stored in the inner space 611. The engaging means is an annular recess 54 as shown in FIG. 2 in case of the closing member 62 arranged on the outer periphery of the proximal end portion of the protecting member 61 that is in the inwardly urged state, that is, the partly cut annular member or the annular member formed from an elastic material, and is an annular projection (not shown) arranged, for example, on the proximal side with respect to the closing member 64 in the case of the closing member 64 that is arranged on the outer periphery of the proximal portion of the protecting member 61 in a natural state.

Hereinafter, with the example of the protector 6 in which the closing member 62 is the partly cut annular member or the annular member formed of the elastic material, a procedure to fixedly engage the outer needle hub 5 and the protector 6 using the annular recess 54 will be described in detail while also explaining how to use the indwelling needle assembly 1 according to the present invention with reference FIG. 1, FIG. 2 and FIG. 8.

As shown in FIG. 1, the proximal end portion of the inner needle 2 is inserted from the distal side of the protector 6 in sequence from the distal opening 612 and the proximal opening 613 of the protector 6, and then the proximal end portion of the inner needle 2 and the inner needle hub 3 are fixed with an adhesive agent or the like, so that the protector 6 is arranged on the inner needle 2 adjacent to the inner needle hub 3. Then, the inner needle 2 and the inner needle hub 3 provided with the protector 6 are inserted into the outer needle 4 from the proximal end portion of the outer needle hub 5. When the flange 31 of the inner needle hub 3 comes into contact with the flange 53 of the outer needle hub 5, the needle point 21 of the inner needle 2 projects from the distal side of the outer needle 4, and hence assembly of the indwelling needle assembly 1 is completed. In this state, the inner needle hub 3 and the outer needle hub 5 may be detachably fixed by a free-lock mechanism such as a coupler.

During the assembly operation of the indwelling needle assembly 1, the closing member 62 of the protector 6 is arranged on the outer periphery of the proximal end portion of the protecting member 61, and the displaceable side wall 63 does not close the distal opening 612. Therefore, the inward urging force of the displaceable side wall 63 is not applied directly to the outer peripheral surface of the inner needle 2, and hence arrangement of the protector 6 according to the present invention on the inner needle 2 is easily achieved. Even when the closing member 62 is arranged in a state of being urged inward, since the proximal end portion of the protecting member 61 has rigidity which does not transmit an inward urging force to the inner needle 2, difficulty of arrangement of the protector 6 on the inner needle 2 is avoided.

After the indwelling needle assembly 1 is pricked into the patient's blood vessel, the inner needle 2 is pulled out from the outer needle 4, and only the outer needle 4 is left in the patient's blood vessel. The indwelling needle assembly 1 according to the present invention is provided with the annular recess 54 as the means for engaging the closing member 62 on the inner peripheral surface of the outer needle hub 5 so as to protect the needle point 21 with the protector 6 at the same time as withdrawing the inner needle 2.

When pulling out the inner needle 2, the inner needle hub 3 is pulled toward the proximal side in a state in which the outer needle 4 and the outer needle hub 5 are fixed to the patient, so that the inner needle 2 is moved toward the proximal side in the outer needle 4. At this moment, the closing member 62 is fixedly engaged with the annular recess 54 provided on the inner peripheral surface of the outer needle hub 5 and the closing member 62 and the protecting member 61 are in frictional engagement. Thus, there is no probability of movement of the protector 6 toward the proximal side with the inner needle 2.

Figure 8A:
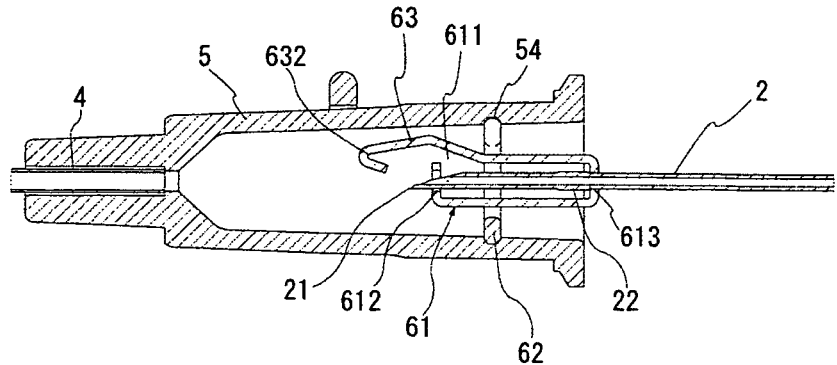
FIGS. 8(a)-8(c) are explanatory drawings illustrating a procedure in which the needle point of the inner needle is stored in the protector when the inner needle is pulled out in the indwelling needle assembly shown in FIG. 1.
Figure 8B:
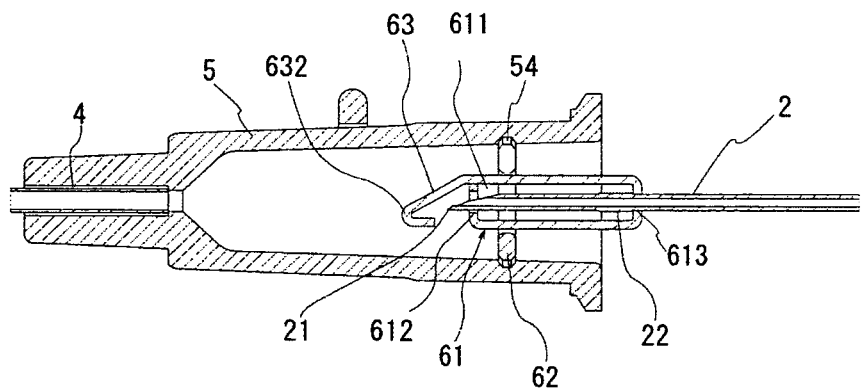
Figure 8C:
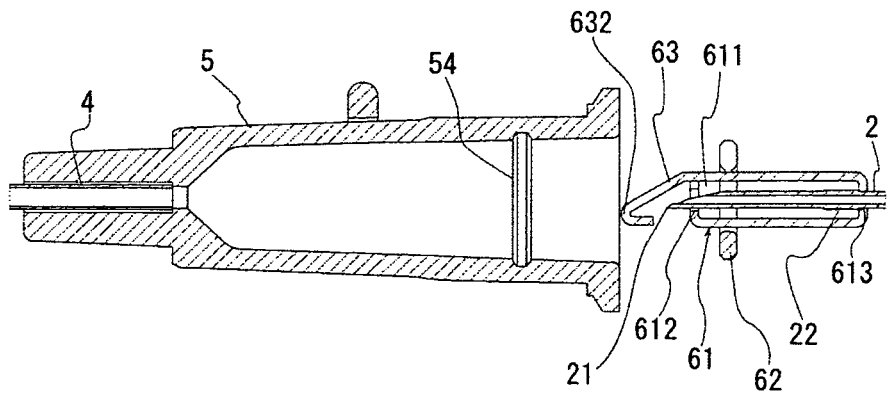

When the needle point 21 of the inner needle 2 is stored in the inner space 611 of the protecting member 61 of the protector 6 and the engaging portion 22 of the inner needle 2 engages the proximal wall 614 of the proximal opening 613 portion of the protecting member 61, as shown in FIG. 8(a), the protecting member 61 moves toward the proximal side with the inner needle 2 from then on. However, the closing member 62 does not move because it is fixedly engaged with the annular recess 54 of the outer needle hub 5. Therefore, the closing member 62 slides on the outer periphery of the protecting member 61 toward the distal side, and is arranged on the outer periphery of the distal end portion of the protecting member 61 provided with the displaceable side wall 63. Then, when the closing member 62 is slid to the distal end portion of the protecting member 61 where the groove area 633 is provided, the closing member 62 is contracted inward and is released from the annular recess 54 of the outer needle hub 5 as shown in FIG. 8(b), and, simultaneously, is fitted into the groove 633 of the protecting member 61 and is locked into the protecting member 61. Accordingly, the fixed engagement between the outer needle hub 5 and the protector 6 is released and, as shown in FIG. 8(c), pulling out of the inner needle 2 from the outer needle 4 and the outer needle hub 5 is completed in a state in which the needle point 21 is protected by the protector 6.

Although use of the indwelling needle assembly 1 according to the present invention has been described with reference to the protector 6 as a partly cut annular member or an annular member formed of an elastic material, it is also possible to reliably protect the needle point 21 of the inner needle 2 by the same operation when the protector 6 provided with the closing member 64 arranged at the proximal end portion of the protecting member 61 is in a natural state, i.e., a state of not being inwardly urged. When using the protector 6 provided with the closing member 64, the outer needle hub 5 and the protector 6 are fixedly engaged by an annular projection instead of the annular recess 54, as shown in the drawings. The annular projection is arranged on the inner peripheral surface of the outer needle hub 5 on the proximal side with respect to the closing member 62 in a state before the needle point 21 of the inner needle 2 is stored in the inner space 61 of the protecting member 61, as shown in FIG. 2. The annular projection prevents the closing member 62 from moving when pulling out the inner needle 2 to a position as shown in FIG. 8(b). However, in the state after the needle point 21 is stored shown in FIG. 8(c), the closing member 62 is engaged more firmly than the engagement with the annular projection by the claws 635 and 636 of the protecting member 61, so that the protector 6 can be separated from the outer needle hub 5 together with the inner needle 2.

When the protector 6 according to the present invention also includes the second locking means which locks the closing members 62 and 64 with the proximal end portion of the protecting member 61, the operation to protect the needle point 21 of the inner needle 2 described above is reliably achieved by setting the shape so that the engaging force between the closing member 62 and the annular recess 54 or the closing member 64 and the annular projection is stronger than the engagement by the second locking means between the protecting member 61 and the closing member 62 or 64.

The protector 6 according to the present invention may be used not only for the indwelling needle assembly as described above, but may also be used for other injection needles, for example, a winged needle.

Figure 9A:
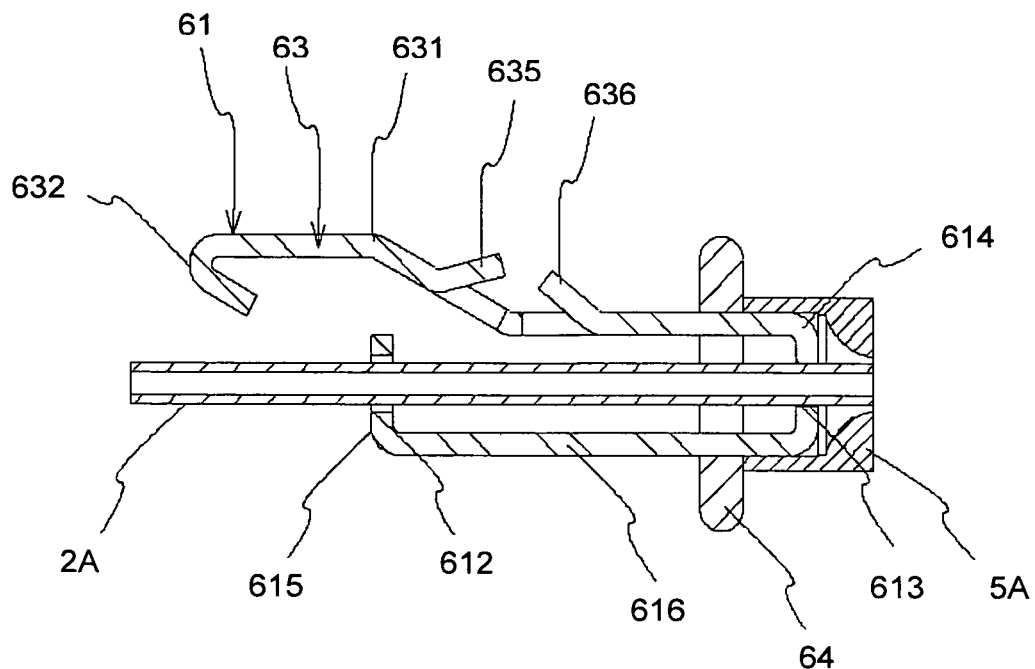
FIGS. 9(a)-9(c) are explanatory drawings illustrating a general example in which the needle point is stored in the protector.
Figure 9B:
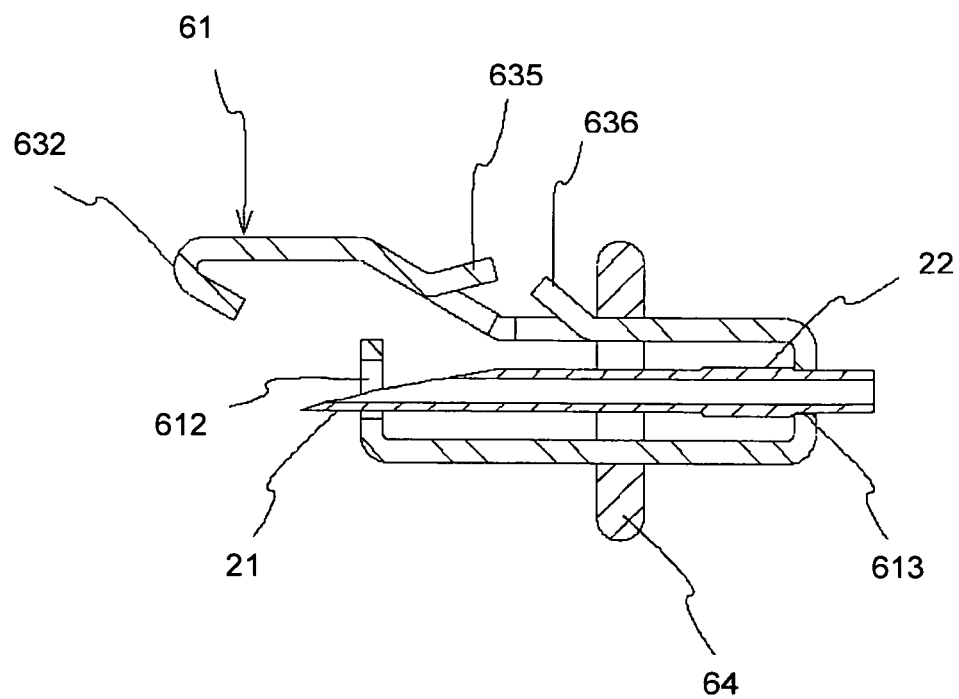
Figure 9C:
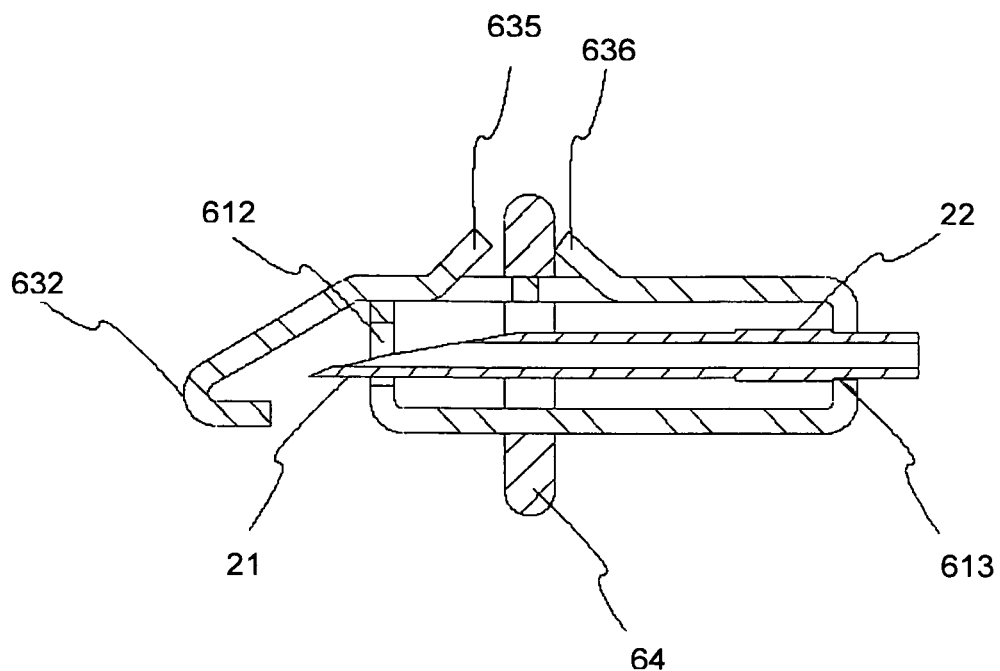
Figure 10:
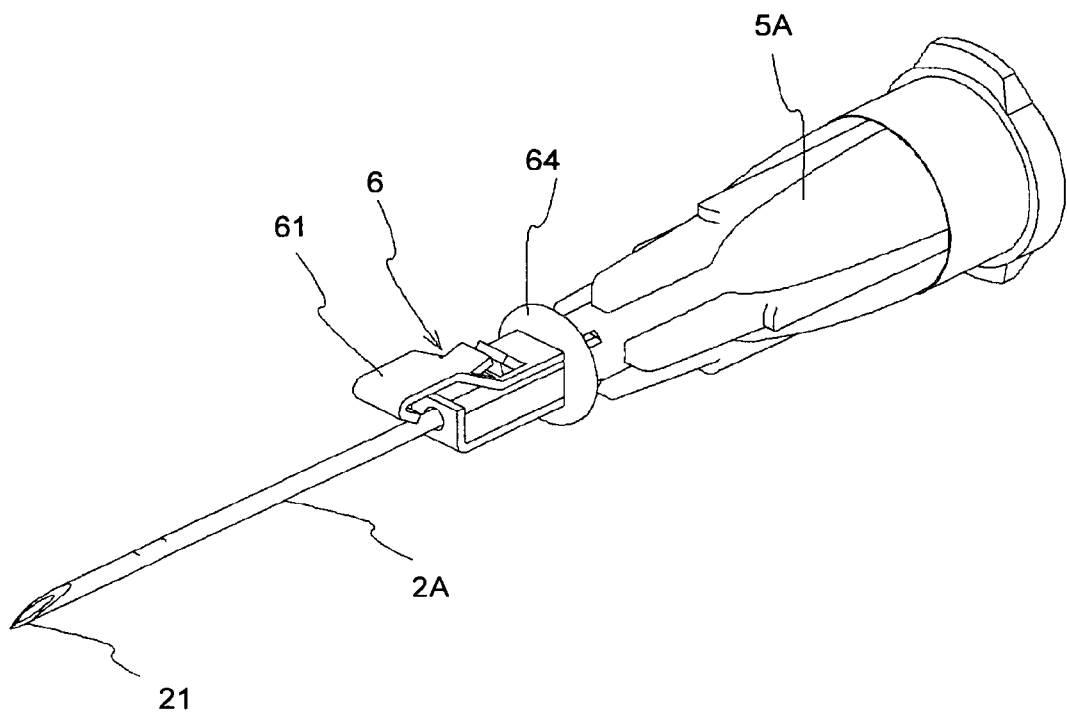
FIG. 10 is a perspective view of an injection needle provided with the protector according to the present invention.

Referring to FIGS. 9 and 10, a general procedure to store the needle point 21 into the protector 6 according to the present invention will be described.

The protector 6 is arranged on the needle 2A of a general injection needle including the needle 2A and a needle hub 5A as shown in FIG. 10 in such a manner that the needle 2A is inserted into the distal opening 612 and the proximal opening 613 in advance before use. The protector 6 according to the present invention allows smooth arrangement of the protector 6 on the needle 2A since the inwardly urging force is not applied directly on the outer peripheral surface of the needle from the displaceable side wall 63 or the closing member 64 in the state before use as shown in FIG. 9(a). The protector 6 may be provided with a holding mechanism such as a concave and convex engagement or caulking on the protector 6 or the needle hub 5A so as to prevent the protector 6 from sliding on the needle 2A after being arranged adjacent to the needle hub 5A on the distal side thereof before the timing when an operation to store the needle point 21 is to be performed.

When protecting the needle point 21 with the protector 6 after having used the needle 2A, the protector 6 is slid on the needle 2A toward the distal side simultaneously with the needle 2A being pulled from a patient's blood vessel or immediately after the needle 2A is pulled out from a patient's blood vessel. At this moment, since the protector 6 according to the present invention is in a state in which the displaceable side wall 63 of the protecting member 61 and the closing member 64 are not inwardly urged or, if inwardly urged, the proximal end portion of the protecting member 61 where the closing member 64 is placed is not deformed by the urging force, the external force is not applied on the needle 2A. Therefore, the medical personnel are able to slide the protector 6 with an extremely light force in comparison with the related art after the needle 2A is used.

When the needle point 21 of the needle 2A is stored in the inner space 611 of the protecting member 61 as shown in FIG. 9(b), the closing member 64 caused to slide on the protecting member 61 toward the distal side. When the closing member 64 reaches the distal end portion of the protecting member 61, the displaceable side wall 63 is inwardly displaced and the distal opening 612 of the protecting member 61 is closed as shown in FIG. 9(c), and hence the needle point 21 is prevented from projecting toward the distal side by the closed portion 632.

In order to prevent the needle point 21 stored in the protector 6 from projecting from the proximal side of the protector 6, it is preferable to form a projection 22 having an outer diameter which does not allow passage through the proximal opening 613 of the protecting member 61 at the distal end portion of the needle 2A to which the protector 6 is attached. When the needle 2A having such the projection 22 is used, the entire length of the protecting member 61 is set so that the needle point 21 is positioned on the proximal side of the closed portion 632 when the projection 22 engages the edge of the proximal opening 613.

This application claims priority of Japanese patent application Nos. 2007-080815 and 2007-171427 filed Mar. 27 and Jun. 29, 2007, respectively, each of which is incorporated herein by reference.

What is claimed is:

1. An indwelling needle assembly comprising:
an inner needle having a sharp needle point at a distal end thereof and an engaging portion in the vicinity of the distal end;
an inner needle hub provided at a proximal end portion of the inner needle;
an outer needle arranged on an outer periphery of the inner needle;
an outer needle hub provided at a proximal end portion of the outer needle; and
a protector for protecting the needle point of the inner needle arranged on the outer periphery of the inner needle so as to be axially slidable, the protector including a protecting member having an inner space which allows storage of the needle point of the inner needle and is slidable axially on the inner needle and a closing member arranged on an outer periphery of the protecting member so as to be slidable from a proximal end to a distal end thereof,
the protecting member including
a distal opening which allows insertion of the inner needle and
a proximal opening which allows insertion of an inner needle body but prevents passage of the engaging portion, and
a displaceable side wall extending outward at a distal portion of the protecting member and which is capable of being displaced inward so as to close the distal opening when the needle point is stored in the inner space of the protecting member provided at the distal end portion thereof, the displaceable side wall being arranged not to contact and being spaced away from an outer peripheral surface of the inner needle in a first position in which the closing member is arranged on an outer periphery of the proximal end portion of the protecting member, and the displaceable side wall displacing inward by the closing member in a second position in which the closing member is arranged on an outer periphery of the distal end portion of the protecting member,
the closing member being arranged on the outer periphery of the proximal end portion on which the displaceable side wall of the protecting member is not provided before the needle point is stored in the inner space of the protecting member, and is configured and adapted to be slid on the outer periphery of the protecting member toward a distal side and to be arranged on the outer periphery of the distal end portion on which the displaceable side wall of the protecting member is provided when the needle point is stored in the inner space of the protecting member.

2. The indwelling needle assembly according to claim 1, wherein the protecting member of the protector includes a proximal wall having the proximal opening and a distal wall having the distal opening and side walls formed integrally with the proximal wall and the distal wall and extending in the axial direction of the needle, the displaceable side wall being provided on part of at least one of the side walls.

3. The indwelling needle assembly according to claim 2, wherein the protecting member of the protector comprises a pair of opposing side walls, and a distal end portion of one of the side walls is the displaceable side wall.

4. The indwelling needle assembly according to claim 2, wherein the protecting member of the protector includes four side walls which surround the needle point from four sides, and a pair of the displaceable side walls is provided at a pair of the distal end portions of opposing side walls.

5. The indwelling needle assembly according to claim 1, wherein the closing member of the protector includes an expansible opening for insertion of the proximal end of the protecting member, said expansible opening having an inner diameter when not expanded that is slightly smaller than the inner diameter required for allowing insertion of the proximal end of the protecting member, and is expanded and arranged on the outer periphery of the proximal end portion of the protecting member in a state of being urged inward.

6. The indwelling needle assembly according to claim 5, wherein the closing member of the protector is a partly cut annular member.

7. The indwelling needle assembly according to claim 5, wherein the closing member of the protector is an annular member formed of an elastic material.

8. The indwelling needle assembly according to claim 5, wherein a locking means is provided at the distal end portion of the protecting member and comprises at least one groove portion which allows engagement with the closing member when the closing member contracts by an urging force.

9. The indwelling needle assembly according to claim 1, wherein the closing member of the protector is an annular member having an opening having an inner diameter which allows insertion of the proximal end of the protecting member, and is arranged on the outer periphery of the proximal end portion of the protecting member without urging the proximal end inwardly.

10. The indwelling needle assembly according to claim 9, wherein a locking means is provided at the distal end portion of the protecting member and comprises a claw projecting outward toward a proximal side and a claw projecting outward toward the distal side.

11. The indwelling needle assembly according to claim 1, wherein engagement between an inner peripheral surface of the outer needle hub and the closing member before the needle point of the inner needle is stored in the inner space of the protecting member is achieved by the closing member engaging with an annular recess formed on the inner peripheral surface of the outer needle hub.

12. The indwelling needle assembly according to claim 1, wherein engagement fixation between an inner peripheral surface of the outer needle hub and the closing member before the needle point of the inner needle is stored in the inner space of the protecting member is achieved by the closing member engaging with an annular projection formed on the inner peripheral surface of the outer needle hub on the proximal side with respect to the closing member.

13. A protector slidable on a needle for protecting a needle point of the needle when the needle is provided in the protector, the protector comprising:
  a protecting member having an inner space for allowing storage of a needle point and openings provided on a distal side and a proximal side for allowing insertion of the needle and being slidable on the needle axially of the needle; and
  a closing member arranged on an outer periphery of the protecting member so as to be slidable from a proximal end a the distal end,
  in which the protecting member includes a displaceable side wall provided at a distal end portion thereof and extending outward, the displaceable side wall being arranged not to contact and being spaced away from an outer peripheral surface of the inner needle in a first position in which the closing member is arranged on an outer periphery of a proximal end portion of the protecting member, and being, displaceable inward thereby closing the opening on the distal side and storing the needle point in the inner space of the protecting member in a second position in which the closing member is arranged on an outer periphery of a distal end portion of the protecting member.

14. The protector according to claim 13, wherein the protecting member includes: a proximal wall having a proximal side opening and a distal wall having a distal side opening; and side walls formed integrally with the proximal wall and the distal wall and extending axially of the needle, and the displaceable aide wall is provided on part of at least one of the side walls.

15. The protector according to claim 14, wherein the protecting member includes a pair of opposing side walls, and a distal end portion of one of the side walls is the displaceable side wall.

16. The protector according to claim 14, wherein the protecting member includes four side walls which surround the needle point from four sides, and a pair of an opposing side walls is provided with a pair of displaceable side walls at the distal end portions thereof.

17. The protector according to claim 13, wherein the closing member is arranged on the outer periphery of the proximal end portion of the protecting member where the displaceable side wall is not provided before the needle point is stored in the inner space of the protecting member, and is slid on the outer periphery of the protecting member toward the distal side and is arranged on the outer periphery of the distal end portion where the displaceable side wall is provided when the needle point is stored in the inner space of the protecting member, and in which the protecting member is provided at the distal end portion thereof with locking means which is capable of preventing further sliding movement when the closing member is arranged on the outer periphery of the distal end portion and maintaining the displaceable wall in a state of being displaced inward.

18. The protector according to claim 13, wherein the closing member is provided with an opening having an inner diameter for allowing insertion of the proximal end of the protecting member, and is arranged on the outer periphery of the proximal end portion of the protecting member in a natural state.

19. The protector according to claim 18, wherein the closing member is an annular member, and a locking means is provided at the distal end portion of the protecting member, the locking means comprising a first claw projecting outward toward the proximal side and a second claw provided on the proximal side of the first claw and projecting outward toward the distal side.

20. The protector according to claim 13, wherein the closing member includes an expansible opening for insertion of the proximal end of the protecting member, said expansible opening having an inner diameter when not expanded that is slightly smaller than the inner diameter required for allowing insertion of the proximal end of the protecting member, and is arranged on the outer periphery of the proximal end portion of the protecting member in a state of being urged inward by an inner periphery thereof being expanded outward.

21. The protector according to claim 20, wherein the closing member is an annular member formed of an elastic material and a locking means is provided at the distal end portion of the protecting member, the locking means comprising at least one recess which allows the closing member contracted by an urging force to fit therein.

22. The protector according to claim 20, wherein the closing member is a partly cut annular member and a locking means is provided at the distal end portion of the protecting member, the locking means comprising at least one recess which allows the closing member contracted by the urging force to fit therein.

* * * * *